United States Patent [19]

Gross

[11] Patent Number: 5,226,898

[45] Date of Patent: * Jul. 13, 1993

[54] CATHETER ADAPTER WITH STRAIN RELIEF

[75] Inventor: James R. Gross, Wareham, Mass.

[73] Assignee: The Kendall Company, Mansfield, Mass.

[*] Notice: The portion of the term of this patent subsequent to Oct. 1, 2008 has been disclaimed.

[21] Appl. No.: 532,047

[22] Filed: May 25, 1990

Related U.S. Application Data

[63] Continuation-in-part of Ser. No. 400,859, Aug. 30, 1989, Pat. No. 5,053,015.

[51] Int. Cl.⁵ .............................................. A61M 5/178
[52] U.S. Cl. ..................................... 604/243; 604/283
[58] Field of Search ............... 604/165, 167, 169, 178, 604/240–243, 256, 283, 905; 285/321, 330, 360, 386, 921, 334.3, 334.4, 332.1, 332.2, 334.1, 334.2, 350; 138/96 T

[56] References Cited

U.S. PATENT DOCUMENTS

| | | | |
|---|---|---|---|
| 1,253,065 | 1/1918 | Looze | 285/360 |
| 2,174,105 | 9/1939 | Haury | 285/350 |
| 2,211,776 | 8/1940 | Haury | 285/350 |
| 4,187,848 | 2/1980 | Taylor | 604/280 |
| 4,613,329 | 9/1986 | Bodicky | 604/158 |
| 4,842,592 | 6/1986 | Caggiani et al. | 604/283 |
| 4,857,062 | 8/1989 | Russell | 604/256 |
| 4,886,507 | 12/1989 | Patton et al. | 604/284 |
| 4,929,243 | 5/1990 | Koch et al. | 604/283 |

Primary Examiner—John D. Yasko
Assistant Examiner—Anthony Gutowski
Attorney, Agent, or Firm—Alvin Isaacs

[57] ABSTRACT

An adapter for a catheter having a body member having a bore and a distal opening, an elastic compression member received in the bore of the body member, with the compression member having a channel extending therethrough to receive the catheter and a distal end extending from the opening of the body member to provide a strain relief for the catheter.

6 Claims, 2 Drawing Sheets

CATHETER ADAPTER WITH STRAIN RELIEF

CROSS REFERENCE TO RELATED APPLICATION

The present application is a continuation-in-part of application Ser. No. 400,859, filed Aug. 30, 1989, now U.S. Pat. No. 5,053,015 issued Oct. 1, 1991.

BACKGROUND OF THE INVENTION

Continuous spinal anesthesia procedures and continuous epidural anesthesia procedures are of course well known in the art. In either case, the distal end of the catheter is first introduced into the patients body with the proximal or trailing end outside the body to receive the anesthetic.

To do so, an adapter is employed connecting the proximal end of the catheter at one end of the adapter to a source of liquid anesthetic, e.g. a syringe, at the other. The adapter has a channel communicating with the catheter end so that when the liquid anesthetic is introduced into the channel, it passes through the catheter into either the subarachnoid space, if the spinal anesthesia procedure is used or into the epidural space, as would be the case with the epidural anesthesia procedure.

As an illustration of prior adapters for this purpose, mention may be made of those described and claimed in U.S. Pat. No. 4,187,848 issued to Glenn N. Taylor. As disclosed therein, the adapter comprises two separate members, one being designated as the body member, the other being termed a compression member. The body member has an elongated bore and an opening at its distal end for receiving the proximal end of the catheter extending from the patient's body. An elongated elastic plug having a channel extending therethrough is seated in uncompressed condition within the bore of the body member, the channel being aligned with the opening of the body member so that the catheter end inserted in the opening can be positioned within the plug channel. The compression member has a port at its proximal end where the tip of a syringe may be releasable engaged for injecting liquid anesthetic. A passageway for fluid extends between the two ends of the compression member so that when the proximal end of the body member and the distal end of the compression member are secured together, the liquid anesthetic injected from the syringe may be pumped into the catheter. To connect the two members, the proximal end of the body member is provided with external threads and the distal end of the compression member with internal threads mating with the body member threads. When the threads are tightened to secure the two members, the plug is compressed to retain the catheter end positioned therein.

The aforementioned parent application, Ser. No. 400,859, relates to an improved adapter wherein the catheter connector and syringe connector are movably pre-connected with respect to each other from an open position to insert the catheter end and a closed position to secure the catheter in place. Anti-back-off means are provided to retain the connector in the closed position, thereby locking the catheter end in the adapter until released by disengaging the anti-back-off means. In the preferred embodiment, means are also provided for preventing overtightening of the connector, which overtightening will cause excessive compressive force to be exerted on the catheter, causing unwanted lowering of its gap through which the anesthetic must traverse as well as possible damage to the catheter.

In both the adapters of the prior art, as exemplified by the aforementioned U.S. Pat. No. 4,187,848, and the improved newer version described and claimed in the parent application, Ser. No. 400,859, there is an inherent problem of kinking of the catheter at a point just external of where the proximal end of the catheter is engaged within the distal opening of the adapter. This kinking, caused by acute bending of the catheter, can materially diminish if not totally inhibit the flow of liquid anesthetic through the catheter.

It is to this kinking problem to which the present invention is directed.

BRIEF DESCRIPTION OF THE INVENTION

In accordance with this invention, the task is solved in an elegant manner by providing an adapter of the foregoing description having a bore and a distal opening, an elastic compression member received in the bore of the body member, with the compression member having a channel extending therethrough to receive the catheter, the essence of the invention being the improvement wherein the distal opening of the bore is enlarged sufficiently so that when compression is applied to the elastic compression member, it causes the distal end of the compression member to extrude through the bore opening to provide a strain relief for the catheter, which strain relief obviates the kinking problem.

DETAILED DESCRIPTION OF THE INVENTION

As mentioned, adapters for continuous spinal or epidural catheters previously in use were of a two-piece construction.

Figures 1, 2:
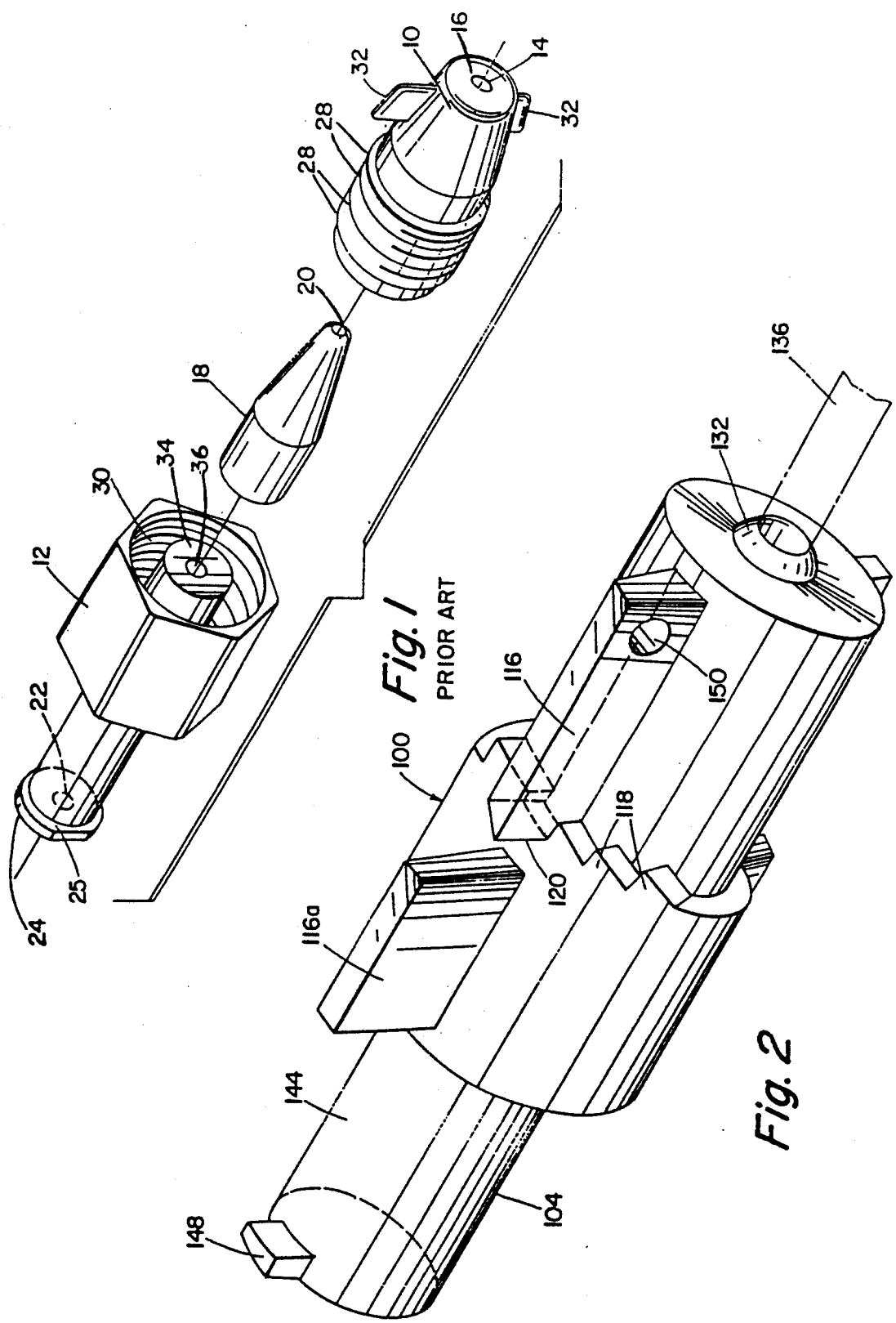
FIG. 1 is a fragmentary exploded elevational view of a two-piece catheter adapter to which this invention is directed.
FIG. 2 is a perspective view illustrating the one-piece adapter described in the parent application, Ser. No. 400,859.

FIG. 1, which need not be described in great detail for purposes of understanding the nature and objects of this invention, is illustrative of the adapters previously in use for the administration of spinal anesthesia.

As shown therein, the adapter consists of two separate body members which, for ease of reference, will be designated as catheter connector 10 and syringe connector 12. Both connectors have a longitudinally extending passageway for pumping the anesthetic from the syringe into the catheter. Catheter connector 10 has an opening 14 at its distal end 16. A compressible plug 18 of elastomeric material having a longitudinally extending channel 20 is seated within a correspondingly shaped bore within connector 10 in a relatively uncompressed condition with channel 20 aligned with opening 14 to receive the proximal end of a catheter (not shown) extending from the body of a patient.

Syringe connector 12 has a tapered port 22 at its proximal end 24 to receive the top of a syringe (not shown). The proximal end 24 has luer lock flanges 25 adapted to receive the luer tip of the syringe so that the syringe may be releasably locked to connector 12.

Connector 10 has external threads 28 adjacent its proximal end which mate with internal threads 30 adjacent the distal end of syringe connector 12.

When the respective connectors are screwed together, e.g. by rotating wings 32 on catheter connector 10, a compression collar 34 having an opening 36 compresses plug 18 to decrease the external dimensions (gap) of channel 20 to secure the catheter end in the adapter.

In use, the distal end of the catheter is first positioned in the patient in per se known manner. The proximal end of the catheter is inserted in the catheter connector and the two connectors are then screwed tightly together to "lock" the catheter in the adapter. The anesthesia procedure may then commence by engaging the syringe in the syringe connector and injecting the liquid anesthetic.

A major disadvantage in adapters of this general description is the tendency for back-off wherein the threads loosen or unscrew to release the compressive force sufficiently for the catheter to be displaced from the adapter. [Since the compression applied should never be so great as to materially narrow the gap of the catheter, substantial drop in compressive force is not required for loss of the catheter connection to occur.]

Another problem is the human factor involved in screwing the two separate connectors together. The parts are relatively small and extremely light. It is very easy to drop one or the other during the manual manipulative step of joining them together. If this should occur, the rigid operating room requirements for aseptic instruments demand that the dropped connector be discarded. This in turn requires the time and expense of opening a new sterile spinal tray to obtain a replacement.

The parent application is directed to a novel adapter which obviates these problems.

Figure 4:
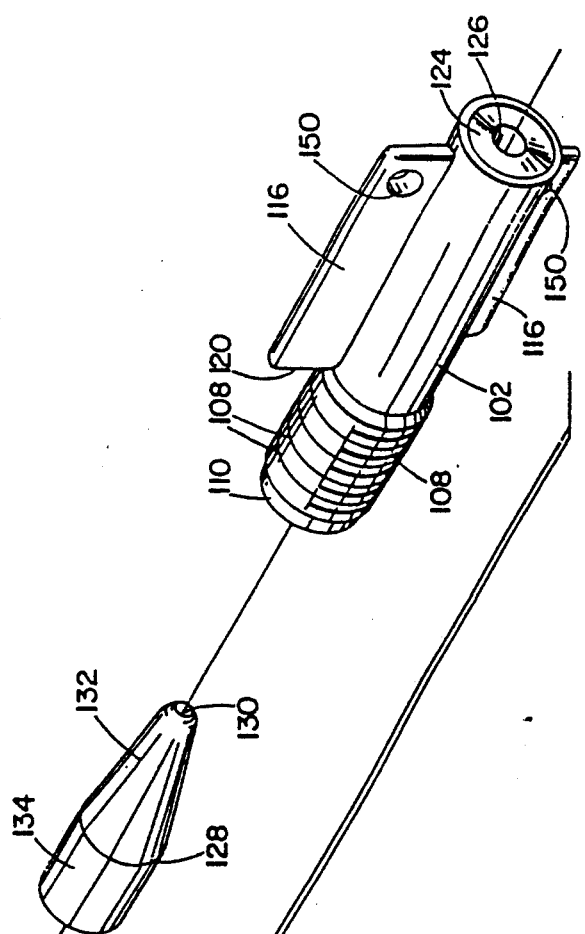
FIG. 4 is a fragmentary top view illustrating the locking mechanism for securing the adapter in the closed position, as shown in FIG. 2
Figure 4:
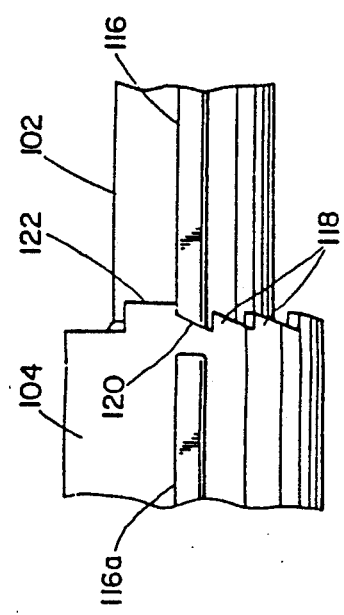
Figure 3:
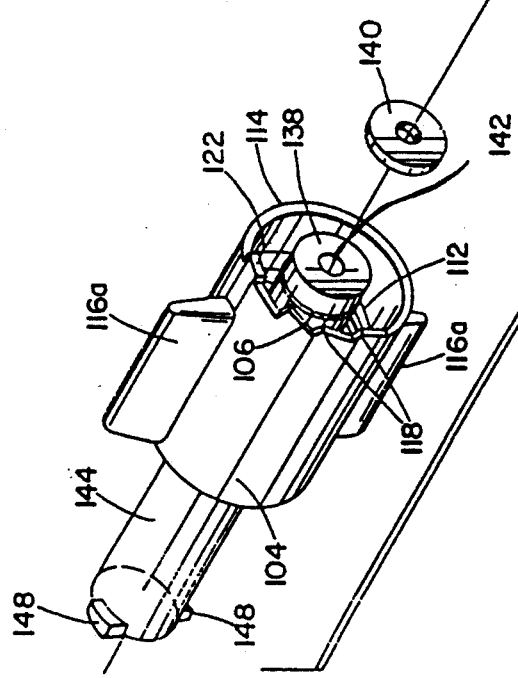
FIG. 3 is an exploded elevational view of the adapter of FIG. 2 illustrating the anti-kinking strain relief of this invention when the adapter is in the closed position.

FIGS. 2-4 illustrate the novel adapter of the parent application.

As shown, adapter 100 has a catheter connector housing 102 (similar to that shown in FIG. 1) and a syringe connector housing 104 which are secured in juxtaposition as a unitary device by means of an external snap ring 106 which engages an internal snap ring (not shown) at the proximal end 110 of catheter connector 102 to prevent separation of the respective housings.

Catheter connector 102 has a series of external threads 108 adjacent its proximal end 110 which mate with internal threads 112 at the distal end 114 of the syringe connector housing 104. By tightening or loosening the connection, e.g. by gripping one of wings 116 or 116a and rotating the other, the connectors are movable longitudinally with respect to each other from a closed position wherein all the threads are engaged (to secure the catheter) to an open position (for insertion or removal of the catheter, as the case may be). When in the open or unthreaded position, the connectors are retained together by snap ring 106, as previously mentioned.

As seen, a portion of distal end 114 of the syringe connector has teeth 118. When screwed together, a locking wing edge 120 interferes with the course of the ratchet-type teeth 118, preventing the connectors from accidentally unscrewing and thereby releasing the catheter from connector 102. In other words, the teeth cooperate with the locking wing edge 120 to prevent back-off and thus lock the respective connectors in the closed position until intentionally disengaged to release the catheter. To prevent overtightening which could cause detrimental excessive compression to be exerted on the catheter, a full stop detent member 122 is preferably provided.

As was the case with the prior art adapters such as illustrated in FIG. 1, catheter connector 102 is generally cylindrical and has an elongated bore. The distal end 124 has a central opening or port 126 through which the proximal (training) end of a catheter extending from the patient's body may be inserted.

An elongated plug 128 of elastomeric material (e.g. natural rubber, synthetic rubber, or an elastomeric polymer such as one of the KRATON (trademark of Shell Chemical Company) series having a channel 130 is seated within connector 102. Plug 128 has a distal conical section 132 and a proximal cylindrical section 134. The portion of the bore in which the plug is to be received with the end of the cone adjacent opening 126 is of like configuration so that the plug is positioned therein in relatively uncompressed condition with channel 130 aligned with opening 126. Both opening 126 and channel 130 (when the latter is uncompressed) have inner dimensions slightly larger than the outer dimensions of the catheter 136 (FIG. 2) to permit easy insertion through the opening and then into the plug.

When the proximal end of the catheter is so positioned, the wings 116 or 116a are rotated to place the adapter in the closed position with the locking wing edge 120 of the catheter connector abutting detent member 122. In this closed position, teeth 118 lock the two connectors together to prevent loosening or back-off. In this position, compression collar 138 located at the distal end of syringe connector housing 104 applies compressive force to the proximal end of the plug 128, causing it to compress longitudinally to narrow the gap of channel 130, thereby tightly frictionally engaging catheter 130 positioned therein. To prevent damage to the proximal end of the channel 124 in the plug, a slip washer 140 is preferably provided, and prevents the plug from getting twisted.

Compression collar 138 has an opening 142 communicating with a fluid passageway within connector 104 and aligned with washer 140 and channel 130, thereby providing a channel for anesthetic injected into the proximal end of syringe connector 104 to be pumped through the adapter and then into the patient via the positioned catheter for administration of the anesthesia procedure.

To accomplish the anesthesia procedure, syringe connector 104 has a female luer slip 144 to receive the tip of the syringe and to frictionally engage the syringe luer when inserted therein. Luer locking wings 148 are provided for engagement to luer locking syringes.

The materials which may be utilized in the manufacture of the adapter of this invention will be readily apparent to those skilled in the art and as such will be a matter of individual choice. Accordingly, they are not critical and per se comprise no part of this invention. In general, with the exception of the elastomeric plug, any of the known plastics which are substantially rigid and of medical grade for use in surgical procedures may be utilized.

In like manner, the method of manufacture will be readily suggested and is accordingly not a part of this invention. Injection molding or any of the other known industrial manufacturing techniques may be employed.

It will be appreciated that the foregoing description is by way of illustration only that various changes, modifications and additions may be made therein.

For example, the wings 116 on connector 102 are shown to have holes 150, the purpose of which is to accommodate a safety pin, suture or other such fastening means to secure the adapter to a sheet, patient's garment or other article, if found desirable or expedient to do so.

While a toothed edge has been shown as the locking mechanism to secure the connectors against back-off, it will be appreciated that other locking means equivalent in function may be provided.

In like manner, any of the per se known means for placing the syringe or other source of fluid medication in engagement with the syringe connector may be employed, e.g. the outwardly directed luer flange described in the aforementioned U.S. Pat. No. 4,187,848.

In accordance with the present invention, the distal opening for receiving the catheter of either the two-piece adapter of FIG. 1 or the one-piece adapter of FIGS. 2-4 is of sufficient diameter to permit extrusion of the plug tip when compressive pressure is applied, thereby providing a strain relief for the catheter.

While the novel feature of this invention is shown, for purposes of illustration, in FIG. 2, it is to be expressly understood that it is equally applicable to the two-piece adapter of FIG. 1.

With reference to FIG. 2, it will be seen that, in accordance with the present invention, when the plug is compressed, the tip of the conical section 132 extrudes through opening 126, thereby providing a strain relief collar for the catheter, such that the distal end of the plug prevents kinking of the catheter during use.

The diameter of opening 126 will in part be dependent upon the external diameter of the plug tip to be extruded therethrough and will in part be dependent upon the compressive force exerted on the plug when the adapter is in the closed position to secure the catheter. Accordingly, it is not capable of precise quantification. The selection of the desired diameter of the distal opening of the adapter for a particular device will, in any event, be within the expected judgment of the skilled worker in the light of the foregoing description. However, by way of illustration, the internal diameter of the proximal end of the connector housing 102 may be 0.200 inch and may taper to the distal port 126 having an internal diameter of 0.100 inch. The plug may then have a proximal end having an outer diameter of 0.200 inch which extends to a distal end having an outer diameter of 0.127 inch, i.e. 0.027 inch greater in the uncompressed state than the internal diameter of distal port 126.

While reference throughout the foregoing specification has been made to anesthetic procedures utilizing a syringe to introduce liquid anesthesia into a spinal or epidural catheter, the primary task of this invention, it is to be expressly understood that the invention is not restricted to such procedures. It may be utilized in other catheterization procedures where a liquid vehicle is introduced via a catheter, which procedures require the catheter to be in fluid communication with a syringe or other source of a liquid drug or other medication.

The foregoing detailed description is given for clearness of understanding only and no unnecessary limitations should be understood therefrom, as modifications will be obvious to those skilled in the art.

What is claimed for:

1. A unitary adapter for placing the proximal end of a catheter which has been inserted in a patient's body in liquid communication with a source of a liquid to be administered to said patient by means of said catheter, said adapter comprising:

a catheter connector housing having distal and proximal ends, said distal end having an opening through which said proximal end of said catheter may be inserted, said catheter connector housing having an internal bore to which said opening communicates;

an elongated elastomeric and compressible plug seated within said bore adjacent said distal end of said catheter connector in a relatively uncompressed condition, said plug having a channel extending therethrough aligned with said opening in said distal end of said catheter housing, whereby said catheter inserted within said opening can extend within said channel, the inner dimensions of said channel when uncompressed and of said opening being slightly greater than the outer dimensions of said catheter to permit insertion of said catheter therewithin;

a connector housing for said liquid source means having proximal and distal ends and a passageway for said liquid extending longitudinally between said ends thereof, said proximal end having means for releasably engaging said liquid source means, said distal end of said source connector housing having an opening communicating with said passageway;

retaining means inseparably retaining said housings together with said proximal end of said catheter connector housing in juxtaposition with said distal end of said source connector housing;

means for reversibly moving said connectors longitudinally with respect to one another from an open, spaced position permitting insertion and withdrawal of said catheter from said catheter connector to a closed abutting position wherein said passageway in said source connector housing, said bore in said catheter connector, said channel in said plug and said catheter when contained therein are in liquid communication to define a closed channel for administering said liquid from said source means to said patient through said catheter; and compression means for compressing said plug when said connector housings are in said closed position, whereby to reduce the gap of said channel and thereby cause said plug to frictionally engage said catheter inserted therein and to retain said catheter in said adapter;

said opening at said distal end of said catheter connector being of sufficient diameter to permit extrusion therethrough of the distal tip of said plug when compressive force is applied by said compression means when said connector housings are in the closed position, thereby providing a strain relief for said catheter, whereby to prevent kinking.

2. An adapter as defined in claim 1 wherein the means for reversibly moving the connectors comprises threads on said proximal end of said catheter connector housing mating with threads on said distal end of said liquid source means connector housing, whereby said housings can be screwed together to provide said closed position and unscrewed to said open position.

3. An adapter as defined in claim 2 including detent means for limiting how tightly together said housings may be screwed.

4. An adapter as defined in claim 3 wherein said liquid source connector has ratchet-type teeth at its distal end and said catheter connector housing includes a locking wing on the external surface thereof, the proximal edge of said locking wing engaging one of said teeth when said connectors are screwed together to said closed position, said locking wing thereby interfering with a course of said ratchet-type teeth, and thereby preventing accidental unscrewing of said connectors towards said open position.

5. An adapter as defined in claim 1 including locking means for securing said connectors in said closed position, whereby to prevent accidental movement toward said open position.

6. An adapter as defined in claim 1 wherein the external diameter of the distal end of said plug in the uncompressed state is greater than the internal diameter of said opening at said distal end of said catheter connector.

* * * * *